(12) United States Patent
Liu et al.

(10) Patent No.: US 6,316,497 B1
(45) Date of Patent: Nov. 13, 2001

(54) SELF-EMULSIFYING SYSTEMS CONTAINING ANTICANCER MEDICAMENT

(75) Inventors: Rong Ron Liu, Gurnee, IL (US); Zheng Wang, Westboro, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/874,622

(22) Filed: Jun. 5, 2001

Related U.S. Application Data

(63) Continuation of application No. 09/339,595, filed on Jun. 24, 1999, now abandoned
(60) Provisional application No. 60/090,452, filed on Jun. 24, 1998.

(51) Int. Cl.$^7$ .................................................. A61K 31/335
(52) U.S. Cl. ......................... 514/475; 514/937; 514/938; 514/941; 514/943
(58) Field of Search ..................................... 514/475, 937, 514/938, 941, 943

(56) References Cited

U.S. PATENT DOCUMENTS 5,422,363 * 6/1995 Yanai et al. .......................... 514/410
5,846,562 * 12/1998 Yanai et al. .......................... 424/451

* cited by examiner

Primary Examiner—Frederick Krass
(74) Attorney, Agent, or Firm—B. Gregory Donner; Gregory Steele

(57) ABSTRACT

The present invention relates to a stabilized self-emulsifying system, comprising a therapeutically effective amount of o-(chloroacetylcarbamoyl)fumigillol, a pharmaceutically acceptable carrier and a stabilizing component, wherein the pharmaceutically acceptable carrier comprises an oily constituent and at least one surfactant. The stabilizing component comprises from about 1% to about 15% water relative to the weight of the self-emulsifying system, an acid, an adsorbent, or a complex-forming agent.

10 Claims, No Drawings

SELF-EMULSIFYING SYSTEMS CONTAINING ANTICANCER MEDICAMENT

This application is a continuation of co-pending U.S. application Ser. No. 09/339,595, filed Jun. 24, 1999, now abandoned, which claims priority to provisional U.S. application Ser. No. 60/090,452, filed Jun. 24, 1998, now abandoned.

TECHNICAL FIELD

The present invention relates to a stabilized self-emulsifying system comprising anticancer medicament. The claimed invention is suitable for formulation of angiogenesis inhibitor o-(chloroacetylcarbamoyl)fumagillol.

BACKGROUND OF THE INVENTION

Fumagillins are a class of compounds naturally secreted from *aspergillus fumigatus* fungus. Synthetic analogues of fumagillins provide a class of angiogenesis inhibitors that exhibit potent anti-angiogenic activity and low systemic toxicity. A synthetic derivative of fumagillin having a formula (I):

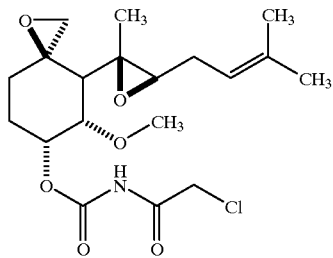

has been described in European Patent No. 0 359 036 and European Patent No. 0 357 061 as having inhibitory effect of suppressing the proliferation of endothelial cells and inhibiting neovascularization. The compounds having angiogenesis inhibiting activity have use in treating tumors in cancerous conditions. (*Cancer Medicine*, 3d. edition, Lea & Febiger, Philadelphia (1993)).

Developing stable formulations for delivering effective amounts of medicament to target organs presents unique challenges in obtaining a suitable formulation for the medicament. Characterized by their lipophilic properties and low water solubility, these drugs typically result in formulations producing low oral bioavailability. European Patent No. 0 602 586 discloses a pharmaceutical composition comprising a fumagillol derivative and a fatty acid ester of glycerin or polyglycerin. Typical formulations are less effective for delivery of the medicament to the angiogenic tumors due to low oral bioavailability of the medicament in the formulation.

Recent developments in drug formulation have resulted in self-emulsifying drug systems (SES) being used as vehicles for orally administering lipophilic medicaments. (Charman, *Pharmaceutical Research*, 39(1): 87–93 (1992)). Self-emulsifying systems are generally recognized to be mixtures of oil and surfactant which, upon exposure to aqueous media, form isotropic dispersions stabilized by an interfacial film of surfactant molecules.

Several self-emulsifying systems containing active drug in mixtures of oil and surfactant, which emulsify and form dispersions under gentle agitation, have been described using various components and for numerous uses.

European Patent No. 0 517 412 describes an oil-based self-emulsifying formulation containing benzodiazepine compounds useful for treating pain, panic, or anxiety.

The self-emulsifying systems described in Shah, *Intl. J. of Pharm.*, 106:15–23 (1994) contain polyglycolized glyceride oils with varying fatty acid and polyethylene glycol.

Pouton, et al., *Intl. J. of Pharm.*, 27:335–348 (1985), discloses self-emulsifying systems containing Miglyol 812 or Miglyol 840 oils in combination with Tween 85 surfactant.

Pharmaceutical formulations wherein the composition is in the form of a self-emulsifying system have particularly advantageous properties with respect to the above fumagillol derivative. Formulations of fumagillin anticancer agents in typical self-emulsifying systems rapidly degrade if formulated without a suitable stabilizing component. Therefore, there continues to be a need to provide effective methods of formulating fumagillin anticancer agents to ensure more effective bioavailability and wider availability of the desired medicaments.

SUMMARY OF THE INVENTION

The present invention relates to a stabilized self-emulsifying system, comprising a therapeutically effective amount of o-(chloroacetylcarbamoyl)fumigillol, a pharmaceutically acceptable carrier, and a stabilizing component, wherein the pharmaceutically acceptable carrier comprises an oily constituent and at least one surfactant. In one aspect of the invention, the stabilizing component of the self-emulsifying system comprises from about 1% to about 15% water relative to the weight of the formulation. Another aspect of the invention relates to a self-emulsifying system comprising a therapeutically effective amount of o-(chloroacetylcarbamoyl)fumigillol and a pharmaceutically acceptable carrier stabilized by an acid. Yet another aspect of the present invention relates to a stable system for active medicament, comprising a self-emulsifying system comprising medicament, a pharmaceutically acceptable carrier, and a stabilizing component, wherein the stabilizing component is an adsorbent or complex-forming agent.

DETAILED DESCRIPTION OF THE INVENTION

The present invention relates to a stabilized self-emulsifying system for medicaments having anticancer activity. The invention particularly relates to a self-emulsifying system having a stabilizing component to prevent degradation of the active medicament in the formulation. Formulations of the present invention exhibit improved bioavailablity of lipophilic compounds useful against cancer conditions. "Self-emulsifying system" as used herein refers to a physically and chemically stable oily solutions, suspensions, or semisolids which, upon contact in an aqueous medium, form a fine dispersion of oil in aqueous medium wherein the dispersion is stabilized by an interfacial film of surfactant molecules. The aqueous medium can be water or the aqueous physiological fluids of the gastrointestinal system.

The term "emulsion" as used herein refers to a liquid-liquid dispersion wherein the dispersion droplets are stabilized by an interfacial film of surfactant molecules. "Emulsion" as defined herein refers to all such dispersions whether formed by a mixture of nonhomogenous liquids and/or solutions or by introducing a self-emulsifying system as defined above into an aqueous medium.

The term "stabilizing component" as used herein refers to the useful components of the self-emulsifying system that provide chemical and/or physical stability to a self-emulsifying system as defined above. The stabilizing component provides useful materials for stabilizing a formulation described as the self-emulsifying system independent of its contact with an aqueous environment or medium.

Medicaments useful in the compositions of the present invention are a class of compounds naturally secreted from *aspergillus fumigatus* fungus named fumagillins, derivatives, and synthetic analogues thereof. In particular, the medicaments useful in the compositions of the present invention have a formula:

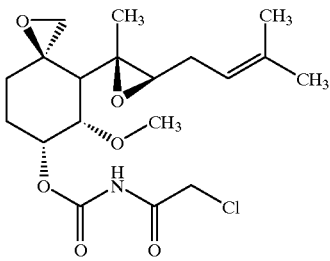

which have been described as having anti-angiogenic activity in the European Patent No. 0 359 036. The medicaments and pharmaceutical formulations containing the medicaments are useful for the treatment of cancer conditions characterized by proliferation of endothelial cells and neovascularization. In particular, the useful medicament is (3R, 4S, 5S, 6R)-5-methoxy-4-[(2R,3R)-2-methyl-3-(3-methyl-2-butenyl)oxiranyl]-1-oxaspiro[2,5]-oct-6yl (chloroacetylcarbamoyl)carbamate or o-(chloroacetylcarbamoyl)fumagillol. The drug typically degrades by hydrolysis under aqueous conditions. The pharmaceutical compositions described herein provide suitable formulations of o-(chloroacetylcarbamoyl)fumigillol in an aqueous environment, such as the stomach of a mammal ingesting the composition, demonstrating an improved oral formulation. Benefits of the claimed formulations include, but are not limited to, the improved solubility of the medicament in solution as well as improved oral bioavailability of the active agent over formulations reported in the scientific literature.

The medicaments useful in the compositions of the present invention include not only those specifically named above, but also where appropriate the pharmaceutically acceptable salts, esters, amides and prodrugs thereof.

"Pharmaceutically acceptable salts, esters, amides and prodrugs" as used herein means those carboxylate salts, amino acid addition salts, esters, amides and prodrugs of a compound which are, within the scope of sound medical judgment, suitable for use in contact with the tissues of humans and lower animals with undue toxicity, irritation, allergic response and the like, commensurate with a reasonable benefit/risk ratio and effective for their intended use. A preferred therapeutic agent is sparingly soluble in water and has solubility in water of less than 5 mg/mL.

The term "pharmaceutically acceptable carrier" refers to a non-toxic solid, semisolid or liquid filler, diluent, encapsulating material or formulation auxiliary of any type. In relation to the present invention, the pharmaceutically acceptable carrier comprises the combination of solvents, surfactants, optional co-surfactants, and stabilizing agents used in the formulation.

Oily components suitable for the process are selected from the group consisting of alcohols, propylene glycol, polyethylene glycol, propylene glycol esters, medium chain mono-, di-, or triglycerides, long chain fatty acids, naturally occurring oils, and a mixture thereof. The oily components suitable for the solvent system include commercially available oils as well as naturally occurring oils. The oils can be characterized as non-surface active oils, which typically have no hydrophile lipophile balance value. Commercially available excipients comprising medium chain triglycerides include, but are not limited to, Captex 100, Captex 300, Captex 355, Miglyol 810, Miglyol 812, Miglyol 818, Miglyol 829, and Dynacerin 660. Propylene glycol ester compositions that are commercially available encompass Captex 200 and Miglyol 840, and the like. The commercial product, Capmul MCM, discloses one of many medium chain mixtures comprising monoglycerides and diglycerides. Suitable naturally occurring oils are seed oils. Exemplary natural oils include oleic acid, castor oil, safflower seed oil, soybean oil, olive oil, sunflower seed oil, and peanut oil. The active medicament generally has greater solubility in commercially available excipients, and therefore, commercially available excipients are preferred over naturally occurring oils as the suitable oil.

Preferably, the oily component comprises medium chain triglycerides or propylene glycol esters. Equivalent compositions whether commercially prepared or prepared according to methods known to those having skill in the art are also suitable for the invention. The most preferred oily component is Captex 200, Miglyol 840, Miglyol 812 or an equivalent composition.

Generally, the surfactants are selected from a group of compounds having a hydrophile lipophile balance (HLB) of less than or equal to 7. Suitable surfactants are selected from a group consisting of propylene glycols, glyceryl fatty acids, glyceryl fatty acid esters, polyethylene glycol esters, glyceryl glycol esters, polyglycolyzed glycerides and polyoxyethyl steryl ethers. Propylene glycol esters or partial esters form the composition of commercial products, such as l,auroglycol FCC, which contains propylene glycol laureate. The commercially available excipient Maisine 35-1 comprises long chain fatty acids, for example glyceryl linoleate. Products, such as Acconon E, which comprise polyoxyethylene stearyl ethers are also suitable for the formulation of the invention. Mixtures of the above named surfactants and compounds are also suitable for the invention. Labrafil M 1944 CS is one example of a suitable surfactant wherein the composition contains a mixture of glyceryl glycol esters and polyethylene glycol esters. These surfactants, mixtures, and other equivalent compositions having an HLB less than or equal to 7 can be used for the formulation of the invention.

Certain surfactants show acceptable compatibility despite having an HLB greater than 7. Generally, acceptable surfactants having an HLB greater than 7 arc used in combination with other surfactant as co-surfactants. Suitable co-surfactants are selected from the group consisting of glyceryl glycol esters, polyethylene glycol esters, polyglycolyzed glycerides, polyoxyethylene glycerol esters, and a mixture thereof. Commercially available co-surfactants based on an oleate or laureate ester of a polyalcohol copolymerized with ethylene oxide are also useful in the invention. Labrasol is a commercially available excipient based on glyceryl glycol esters and polyethylene glycol esters. Gelucire 44/14 comprises polyglycolyzed glycerides. Tween 80 (polysorbate 80) exemplifies a polyoxyethylene sorbitan monooleate suitable as the co-surfactant. Tween 80 and Labrasol are the preferred co-surfactants.

In one aspect, the present invention relates to a stabilized self-emulsifying system comprising the medicament, a pharmaceutically acceptable carrier and a stabilizing component, wherein the stabilizing component is water. In another aspect of the invention, the stabilized self-emulsifying system comprises the medicament, the pharmaceutically acceptable carrier, and a stabilizing component, wherein the stabilizing component comprises an acid. In yet another aspect, the present invention relates to a stabilized self-emulsifying system comprising the medicament, the pharmaceutically acceptable carrier, and a stabilizing component, wherein the stabilizing component comprises an adsorbent or complex-forming agent.

Surprisingly, adding a small amount of water to the oil-based formulation stabilizes the self-emulsifying system. The stabilizing component in the present aspect of the invention comprises from about 1% to about 15% water relative to the weight of the self-emulsifying system. The relative amount of water is critical to the stability of the self-emulsifying system in this aspect of the invention. Presence of excess water causes degradation of the active medicament in the formulation. Moreover, formulations having less than 1% water are unsatisfactory due to instability of the medicament. Chemical stability of the medicament in the self-emulsifying system is accomplished from about 1% to about 15% water. Preferably, the self-emulsifying system contains from about 2% to about 12% water relative to the weight of the formulation. Most preferably, the formulation contains from about 7.0% to about 7.5% water.

The presence of water in the self-emulsifying system will form reverse micelles with surfactants, for example Tween 80 or Capmul MCM. The core of the micelle consists of an aqueous or hydrophilic micro-phase. hydrophilic impurities will be solubilized or partitioned into the reversed micelles in formulation, thereby minimizing the degradation of the o-(chloroacetylcarbamoyl)fumigillol. The formation of reversed micelles in the self-emulsifying system protects the drug from degradation or stabilizes the drug in the macroscopically homogeneous SES solution.

Another stabilizing component useful in the stabilized self-emulsifying system is an acid. Suitable acids for the formulation comprise organic acids as well as inorganic acids and derivatives thereof. Organic acids suitable for the formulation are selected from the group consisting of aliphatic carboxylic acids, aromatic carboxylic acids, and sulfonic acids. Suitable aliphatic carboxylic acids comprise $C_1-C_{16}$ carboxylic acids, including hydroxycarboxylic acids. Exemplary aliphatic carboxylic acids include, but are not limited to, formic acid, acetic acid, propionic acid, butyric acid, valeric acid, caproic acid, enanthic acid, caprylic acid, pelargonic acid, capric acid, lauric acid, myristic acid, palmitic acid, stearic acid, and the like, or a mixture thereof. Hydroxycarboxylic acids are selected from the group consisting of citric acid, glycolic acid, lactic acid, malic acid, and the like, or a mixture thereof. Aromatic organic acids suitable for the formulation are selected from the group comprising benzoic acids and derivatives thereof. Suitable aromatic carboxylic acids and derivatives thereof include, but are not limited to, aminobenzoic acid, benzoic acid, acetylsalicylic acid, salicylic acid, and the like, or a mixture thereof. Additional organic acids include suitable sulfonic acids, such as alkanesulfonic and arenesulfonic acids, which are selected from the group consisting of methanesulfonic acid, 2-propane-sulfonic acid, trifluoromethanesulfonic acid, benzenesulfonic acid, p-toluenesulfonic acid, and the like, or a mixture thereof. Inorganic acids suitable for the invention are selected from the group consisting of orthophosphoric acid, polyphosphoric acid, pyrophosphoric acid, hydrochloric acid and the like, or a mixture thereof. Preferably, the acid used is an organic acid. The preferred organic acid is hydroxycarboxylic acid. Citric acid is the most preferred acid.

Preferably, the acid will comprise between about 0.005% to about 5.0% weight relative to the self-emulsifying system. It is preferred that the acid comprises from about 0.05% to about 1.0% weight of the stabilized self-emulsifying system.

Suitable adsorbents or complex forming agents are selected from the group consisting of gelatin, active charcoal, silica gel, and chelating agents. The pharmaceutically acceptable carrier having the medicament can be filled, mixed, adsorbed, filtered or otherwise combined, contacted, or reacted with the adsorbent or complex forming agent. Exemplary chelating agents are chelates and/or salts of ethylenediaminetetraacetic acid (EDTA). Preferably, the adsorbent is a gelatin, which can be shaped as a capsule, shell, pod, caplet or any other suitable form for containing a liquid self-emulsifying system. The gelatin form can be a hard or soft gelatin capsule.

The adsorbent or complex-forming agent typically comprises from about 0.05% to 15% weight adsorbent or complex-forming agent relative to the weight of the medicament. Preferably, the adsorbent or complex-forming agent comprises from about 0.05 to about 10 weight percent of the total formulation. The exact amount of adsorbent or complex-forming agent can be determined by one having ordinary skill in the art considering the active agent, excipients, and the nature of the stabilizing component in the self-emulsifying system and the amount of material necessary to stabilize the medicament.

The stabilized self-emulsifying systems of the present invention form emulsions upon gentle agitation in an aqueous environment. Droplet sizes of the emulsion preferably have a diameter of less than 25 microns. The preferred droplet sizes are less than 5 microns in diameter. Typically, smaller droplets in the formed emulsion more effectively deliver the active medicament. Droplet size in the formed emulsion can be determined using a Sympatec Helos (H0687) laser diffraction particle sizer. The dispersing system is stirred at a rate of 40 r.p.m. and 0.1 mL of sample is added to 4 mL of water. The sample is shaken for 10 minutes and measured for a measuring time of 10 seconds.

A preferred mixture having the proper ratio of components is described below in Table 1.

TABLE 1

| Emulsion Component | Preferred Proportions |
| --- | --- |
| Oil components | between 20% and 90%, preferably 40% to 60% by weight of the total |
| Surfactant | between 5% and 50%, preferably 20% to 40% by weight of the total |
| Co-surfactants | between 0 and 40%, preferably 4% to 20% by weight of the total |
| Stabilizing agent | at least one of the following in the indicated proportions: preferably 1–15%, and more preferably 2–12%, water by weight of the total; preferably 0.005–5.0%, and more preferably 0.05–1.0%, acid by weight of the total, and preferably more than 0.05–15%, and more preferably 0.05–10%, adsorbent or complex-forming agent relative to the weight of the medicament |

A pharmaceutical composition in accordance with the invention comprises a therapeutically active amount of o-(chloroacetylcarbamoyl)fumigillol, an oily constituent, at least one surfactant, and stabilizing component, wherein the stabilizing component is selected from about 1 to about 15 weight percent water; from about 0.005 to about 5.0 weight percent acid; and from about 0.05 to about 15 weight percent of an adsorbent or complex-forming agent.

A preferred composition of the invention comprises from 40 to about 60 weight percent of the oily component; from 20 to about 40 weight percent surfactant; from about 4 to about 20 weight percent co-surfactant, and from 1 to about 15 weight percent water. A more preferred composition comprises from about 2 to about 12 weight percent water. The most preferred composition comprises from about 7.0 to about 7.5 weight percent water.

Another preferred composition of the invention comprises from 40 to about 60 weight percent of the oily component; from 20 to about 40 weight percent surfactant; from about 4 to about 20 weight percent co-surfactant; and from about 0.05 to about 5.0 weight percent acid. A more preferred composition comprises from about 0.05 to about 1.0 weight percent acid.

Yet another preferred composition of the invention comprises from 40 to about 60 weight percent of the oily component; from 20 to about 40 weight percent surfactant; from about 4 to about 20 weight percent co-surfactant; and from about 0.05 to about 15 weight percent adsorbent or complex-forming agent. A more preferred composition comprises from about 0.05 to about 10 weight percent adsorbent or complex-forming agent.

The compositions of the present invention can comprise additives conventionally used for preparing formulations. Examples of the additives include those used for oral liquid systems and injectable preparations, such as preservatives, antioxidants, and thickening agents. Exemplary preservatives include, but are not limited to, benzylalcohol, ethylalcohol, benzalkonium chloride, phenol, chlorobutanol, and the like. The antioxidants for the invention provide oxygen or peroxide inhibiting agents for the formulation and include, but are not limited to, butylated hydroxytoluene, butylhydroxyanisole, propyl gallate, ascorbic acid palmitate, α-tocopherol, and the like. Thickening agents, such as lecithin, hydroxypropylcellulose, aluminum stearate, and the like, may improve the texture of the formulation.

The pharmaceutical formulations of the present invention optionally can be molded into solid, semisolid or liquid preparations. For such preparations, the composition of the present invention is molded into powder composition as it is or after mixing it with added vehicles, such as glucose, mannitol, starch, microcrystalline cellulose, and the like; thickening agents, such as natural gums, cellulose derivatives, acrylic acid polymers, and the like; and other additives or excipients used in solid or semisolid preparations. For the liquid preparations, oily or aqueous preparations of emulsions formed from the self-emulsifying systems of the invention are prepared according to almost the same manner as that in the above injectable preparations.

To prepare suppositories, the composition of the present invention can be molded into oily or aqueous solid, semi-solid or liquid suppositories by methods known in the art.

In another aspect of the invention, the present invention relates to a method of suppressing cell proliferation and neovascularization comprising administering a formulation having the above stabilized self-emulsifying system. The stabilized self-emulsifying system suitable for an intended mode of administration, such as topical, parenteral, or oral, e.g. in the form of capsule fillings. The term "parenteral" as used herein refers to modes of administration, which include intravenous, intramuscular, intraperitoneal, intracisternal, subcutaneous and intraarticular injection and infusion.

The compositions and methods of the present invention will be better understood in connection with the following Examples. The Examples are intended as illustrations of and not a limitation upon the scope of the invention.

EXAMPLES

Example 1

Preparation of the Stabilized SES Formulation

Example 1a: Captex 200 (propylene glycol dicaprylate/dicaprate; ABITEC Co.), Capmul MCM (medium chain mono and diglyceride; ABITECH Co.), Tween 80 (polysorbate 80; Sigma) were added in a container and mixed well with a magnetic stir bar. The o-(chloroacetylcarbamoyl)fumagillol (EP 0 359 036; Takeda Chemical Industries., Ltd., Tokyo, Japan) was added with stirring until the drug completely dissolved to form a clear, yellowish solution. The final formulations were gently agitated to blend the ingredients. To a base formulation of Captex 200, Capmul MCM, and Tween 80 was added o-(chloroacetylcarbamoyl)fumigillol until the drug was completely dissolved. Water was added to the formulation to obtain a composition having final concentrations of 66.5% Captex 200, 19% Capmul MCM, 9.5% Tween 80, 7.5% water, and 5% medicament wt./wt. based on the total weight of the formulation.

Example 1b: To a base formulation of Labrasol, Miglyol 812, and Lauroglycol FCC was added o-(chloroacetylcarbamoyl)fumigillol until the drug was completely dissolved to obtain a composition having final concentrations of 20% Labrasol, 20% Miglyol 812, 50% Lauroglycol FCC, and 10% medicament wt./wt. based on the total weight of the formulation. The solution was filled into a 200 mg airfill softgell capsule.

Example 1c: To a base formulation of Miglyol 840, Lauroglycol FCC and Tween 80 was added o-(chloroacetylcarbamoyl)fumigillol until the drug was completely dissolved to obtain a composition having final concentrations of 42.5% of Miglyol 840, 42.5% of Lauroglycol FCC, 5% of Tween 80, and 10% of the medicament wt./wt. based on the total weight of the formulation. The solution was filled into a 50 mg airfill softgell capsule shell.

Example 2

Stability of Stabilized SES Formulations Containing Water

A determination of the effect of water on the stability of several SES formulations prepared in accordance with the invention were conducted as follows: Captex 200 (propylene glycol dicaprylate/dicaprate; ABITEC Co.), Capmul MCM (medium chain mono and diglyceride; ABITECH Co.), Tween 80 (polysorbate 80; Sigma) were added in a container and mixed well with a magnetic stir bar. The o-(chloroacetylcarbamoyl) fumagillol (EP 0 359 036; Takeda Chemical Industries., Ltd., Tokyo, Japan) was added with stirring until the drug completely dissolved to form a clear, yellowish solution to prepare a base formulation having final concentrations of 66.5% Captex 200, 19% Capmul MCM, 9.5% T ween 80, and 5% medicament wt./wt. based on the total weight of the formulation. Water was combined in the amounts shown in Table 2 based on the weight of the base formulation. The final formulations were gently agitated to blend the ingredients before the initial stability determination was taken.

Results of these tests are shown below in Table 2. The data obtained showed that water produced a good stabilizing quality in the self-emulsifying systems, with the best results obtained at 7.5%.

TABLE 2

| Amount of Water (% wt./wt.) | k (per day) | t 0.5 (day) | Corr. r. |
|---|---|---|---|
| 0 | 0.351 | 1.976 | 0.9795 |
| 2.5 | 0.082 | 8.413 | 0.9940 |
| 5 | 0.025 | 27.709 | 0.9969 |
| 7.5 | 0.019 | 36.130 | 0.9950 |

Example 3

Stability of Stabilized SES Formulations in Acid

To illustrate the effect of citric acid on the stability of the SES, several formulations were prepared as follows: Citric acid was added to Labrasol (glyceryl and polyethylene glycol esters; Gettefosse) and stirred using a magnetic stir bar at 50° C. until the citric acid dissolved. To the cooled solution, Miglyol 812 (caprylic acid/capric acid triglyceride; Huls America) and Laurolglycol FCC (Gettefosse) were added and mixed well. The o-(chloroacetylcarbamoyl) fumagillol was added with stirring until the drug completely dissolved to produce a final formulation containing concentrations of 20% Labrasol, 20% Miglyol 812, 50% Lauroglycol FCC, and 10% medicament wt./wt based on the total weight of the formulation. The final formulations were gently agitated to blend the ingredients. The formulations were stored at 80° C. for 24 hours before determining the percentage of medicament remaining.

The results of these studies, shown below in Table 3, demonstrate the stabilizing, effect of citric acid on the formulations of the present invention. The percentages of medicament remaining in the respective citric acid formulations at 80° C. are indicated below.

TABLE 3

| | % Citric Acid | | | | |
|---|---|---|---|---|---|
| | 0 | .2 | .4 | .6 | 1.0 |
| % Medicament Remaining | 77.6 | 93.7 | 96.1 | 92.4 | 90.5 |

Example 4

Stability of Stabilized SES Formulations in Gelatin

The effect of gelatin on the stability of several SES formulations prepared in accordance with the invention was determined by studies conducted as follows: Tween 80, Miglyol 840 and Laurolglycol FCC were combined at room temperature and mixed well. The o-(chloroacetylcarbamoyl) fumagillol was added with stirring until the drug completely dissolved to produce a final formulation containing concentrations of 5% Tween 80, 42.5% Miglyol 840, 42.5% Laurolglycol FCC, and 10% medicament wt./wt. based of the total weight of the formulation. The final formulations were gently agitated before the initial stability determination was taken.

To prepare the formulation with gelatin, an opening was formed in the tip of a gelatin capsule and the preparation was injected into the capsule using a Ilamilton gastight teflon glass syringe. Sealing the opening with heat and pinching contained the formulation in the capsule.

The amounts of medicament remaining in the prepared formulation and in the filled capsule were measured. Measurements were taken tinder separate reaction condition at 50° C. and 80° C., respectively. Results of these tests shown below in Table 4 describe the percentage of medicament remaining in the formulation with and without gelatin relative to each set of reaction conditions. The data obtained showed that the gelatin produced a good stabilizing effect on self-emulsifying drug formulations.

TABLE 4

| | Reaction Conditions | |
|---|---|---|
| Prototype | 50° C., 15 days | 80° C., 5 days |
| Formulation without Gelatin | 80.52% | 14.52% |
| Formulation with Gelatin | 90.14% | 52.47% |

Example 5

Stability of Stabilized SFS Formulations in Gelatin

Measurements were also taken under separate reaction conditions in a related study of the formulation stability. The formulation with gelatin was prepared as described above in Example 4. Results of the storage stability for the formulation with gelatin is shown below in Table 5. The results illustrate the percentage of medicament remaining in the formulation per time interval, described in months (M), relative to each set of storage conditions. The data obtained showed that the gelatin produced a long-term stabilizing effect on self-emulsifying drug formulations.

TABLE 5

| | Stability Data | |
|---|---|---|
| Storage Conditions | Interval | % Medicament Remaining |
| Initial | 0 | 100% |
| 5° C. | 1 M | 99.5% |
| | 3 M | 99.0% |
| 25° C./60 RH† | 1 M | 99.0% |
| | 2 M | 98.5% |
| | 3 M | 97.0% |

†RH denotes relative humidity.

Example 6

Bioavailability of the Stabilized SES Formulation

A control group of 5 mice and 3 subject groups of athymic mice with 50 mice per group were treated in the study. The control group was bled before treatment and the plasma from the mice was prepared by mixing 0.1 volumes of 2% sulfuric acid in water. Each of the subject groups, 1, 2, and 3, was treated with a single dose of 50 mg/kg body weight of o-(chloroacetylcarbamoyl)fumagillol (the medicament) administered subcutaneously (in gum arabic solution), orally in gum arabic (2% ethanol/5% gum arabic/93% saline), or orally in a self-emulsifying system, respectively. A self-emulsifying system (10 g) was prepared by combining medicament (0.5 mg) in Captex 200 (6.5 g), Capmul CMC (1.9 g), and Tween 80 (0.95 g). The dosing volume for all mice was 0.1 mL, per 10 grams of body weight. Plasma samples were collected at pre-treatment (control group only)

and at the following time intervals: 15 min., 30 min., 60 min., 90 min., 120 min., 150 min., 3 hrs., 4 hrs., 6 hrs., and 8 hrs. after treatment. At the designated time intervals, 5 mice in each subject group were sacrificed and bled using heparin as an anti-coagulant. Plasma samples taken from the subject group mice were treated in the same manner as indicated for the pretreatment group.

Compilation of the results determining the bioavailability of the o-(chloroacetylcarbamoyl)fumagillol are shown in Table 6 below. Subcutaneous administration in gum arabic solution provides a standard for comparing gum arabic and the SES oral dosage forms. Samples were measured for plasma concentration of the medicament (A), an active metabolite (B), and an inactive metabolite (C).

TABLE 6

| Dosage Form | $C_{max}$ (ng/mL) | $T_{max}$ (hr) | $AUC_{0-8\ hrs.}$ (ng · hr/mL) | Relative Bioavailability (%) |
|---|---|---|---|---|
| Subcutaneous | A: 70.41<br>B: 218.86<br>C: 536.36 | A: 0.4<br>B: 0.3<br>C: 0.3 | A: 30.09<br>B: 116.62<br>C: 329.14 | N/A |
| Oral Solution (Gum Arabic) | A: 1.06<br>B: 14.61<br>C: 148.71 | A: 3.1<br>B: 0.3<br>C: 0.25 | A: 1.11<br>B: 6.93<br>C: 106.46 | A: 3.7%<br>B: 5.9%<br>C: 32.3% |
| Oral SES Formation | A: 5.54<br>B: 11.41<br>C: 51.70 | A: 1.4<br>B: 1.3<br>C: 2.3 | A: 5.40<br>B: 20.57<br>C: 171.90 | A: 17.9%<br>B: 17.6%<br>C: 52.2% |

Example 7

Comparison of Stabilized SES Bioavailability with Oil Formulations

A 50 mg oral dose of o-(chloroacetylcarbamoyl) fumagillol dissolved in a glyceride solution was compared with an SES prepared as described in Example 4. Each dose was orally administered to dog subjects treated in the study. Blood samples were collected at 0, 0.25, 0.5, 1, 1.5, 2, 3, 4, 6, and 9 hours after the dosing. Bioavailability of the drug was assessed by evaluating the plasma level of an o-(chloroacetylcarbamoyl)fumagillol inactive metabolite.

Results of the comparative study illustrate that, for MII, a metabolite of TNP-470 which was used as one the criteria for bioavailability assessment, the SES formulation provides nearly 2.5 times the absolute oral bioavailability (F) of a known oily solution. Summary of the study is shown below in Table 7.

TABLE 7

| Formulation | $C_{max}$ (ng/mL) | $T_{max}$ (hr) | AUC (ng · hr/mL) | F (%) |
|---|---|---|---|---|
| SES | 1111.2 | 1.0 | 2541.3 | 66.7 |
| SD‡ | 153.9 | 0.5 | 752.0 | 7.6 |
| Glyceride Solution | 486.3 | 0.5 | 1069.5 | 26.9 |
| SD | 91.9 | 0.3 | 494.6 | 9.3 |

‡SD denotes the standard deviation of each measurement relative to the mean values.

Example 8

Droplet Size Comparison of Stabilized SES with Oil Formulations

The effect of gelatin on the stability of several SES formulations prepared in accordance with the invention was determined by studies conducted as follows: Tween 80, Captex 200 and Capmul MCM were combined at room temperature and mixed well. The o-(chloroacetylcarbamoyl) fumagillol was added with stirring until the drug completely dissolved to produce a final formulation containing concentrations of 9.5% Tween 80, 66.5% Captex 200, 19% Capmul MCM, and 5% medicament wt./wt. (I).

To the mixture of Tween 80, Captex 200 and Capmul MCM was added 7% wt./wt. water. The o-(chloroacetylcarbamoyl)fumigillol was added with stirring until the drug completely dissolved to product a final formulation containing concentrations of 8.8% Tween 80, 61.6% Captex 200, 17.6% Capmul MCM, and % medicament wt./wt. (II).

The final formulations were gently agitated before the self-emulsifying ability for the SES formulations were taken.

The tip an airfill softgell capsule shell was snipped off and an agitated solution of formula (I) (0.8 mL) was filled into the capsule. The neck of the capsule shell was heated using a heat gun and then immediately sealed by pinching the opening with forceps.

Self-emulsifying formulations I, II and III were agitated and added into a 10 mL test tube containing 4 mL of water as the dispersant. The samples were analyzed for particle size using a laser light scattering particle sizer (HELOS BF. Sympatec GmbH) at a stirring rate of 40 r.p.m.

The mean droplet sizes of the O/W emulsions generated by formulations I and II were 1.48 $\mu$m and 1.60 $\mu$m, respectively. No significant difference in the size was observed between formulations I and II.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the substituents, means or preparation and/or methods of use of the invention, may be made without departing from the spirit and scope thereof.

What is claimed is:

1. A stabilized self-emulsifying system, comprising a therapeutically effective amount of o-(chloroacetylcarbamoyl)fumigillol, a pharmaceutically acceptable carrier and a stabilizing component, wherein the pharmaceutically acceptable carrier comprises an oily constituent selected from the group consisting of alcohols, propylene glycol, propylene glycol esters, poylethylene glycol, monoglycerides, diglycerides, triglycerides, fatty acids, naturally occurring oils, and a mixture thereof and at least one surfactant, and the stabilizing component comprises from about 1% to about 15% water relative to the weight of the stabilized self-emulsifying system.

2. The stabilized self-emulsifying system according to claim 1, wherein the stabilizing component comprises from about 2% to about 10% water.

3. The stabilized self-emulsifying system according to claim 2, wherein the stabilizing component comprises from about 7.0% to about 7.5% water.

4. The system according to claim 1, comprising from 40 to 60 weight percent of the oily component; from 20 to 40 weight percent surfactant; from 4 to 20 weight percent co-surfactant, and from 2 to about 12 weight percent water.

5. The system according to claim 4, wherein the composition comprises from about 7.0 to about 7.5 weight percent water.

6. The system according to claim 1, comprising from 40 to 60 weight percent of the oily component; from 20 to 40 weight percent surfactant; from 4 to 20 weight percent co-surfactant; and from 0.005 to about 5.0 weight percent of an acid.

7. The system according to claim 6, wherein the composition comprises from about 0.05 to about 1.0 weight percent acid.

8. The system according to claim 1, comprising from 40 to 60 weight percent of the oily component, from 20 to 40 weight percent surfactant; from 4 to 20 weight percent co-surfactant; and from 0.05 to about 15 weight percent of an adsorbent or complex-forming agent.

9. The system according to claim 8, wherein the composition comprises from about 0.05 to about 10 weight percent of the adsorbent or complex-forming agent.

10. A method of suppressing cell proliferation and neovascularization comprising administering the self-emulsifying, system of claim 1 to a subject.

* * * * *